US010856763B2

United States Patent
Kiranyaz et al.

(10) Patent No.: US 10,856,763 B2
(45) Date of Patent: Dec. 8, 2020

(54) PERSONALIZED ECG MONITORING FOR EARLY DETECTION OF CARDIAC ABNORMALITIES

(71) Applicant: QATAR UNIVERSITY, Doha (QA)

(72) Inventors: Serkan Kiranyaz, Doha (QA); Turker Ince, Izmir (TR); Moncef Gabbouj, Tampere (FI)

(73) Assignee: QATAR UNIVERSITY, Doha (QA)

( * ) Notice: Subject to any disclaimer, the term of this patent is extended or adjusted under 35 U.S.C. 154(b) by 221 days.

(21) Appl. No.: 15/759,328

(22) PCT Filed: Mar. 10, 2017

(86) PCT No.: PCT/IB2017/051406
§ 371 (c)(1),
(2) Date: Mar. 12, 2018

(87) PCT Pub. No.: WO2018/162957
PCT Pub. Date: Sep. 13, 2018

(65) Prior Publication Data
US 2019/0069795 A1    Mar. 7, 2019

(51) Int. Cl.
*A61B 5/0468*    (2006.01)
*G16H 50/20*    (2018.01)
(Continued)

(52) U.S. Cl.
CPC ........ *A61B 5/0468* (2013.01); *A61B 5/02438* (2013.01); *A61B 5/02455* (2013.01); *A61B 5/04028* (2013.01); *A61B 5/6831* (2013.01); *A61B 5/725* (2013.01); *A61B 5/7225* (2013.01); *A61B 5/7267* (2013.01); *A61B 5/7278* (2013.01); *G06N 3/084* (2013.01); *G16H 40/63* (2018.01); *G16H 50/20* (2018.01)

(58) Field of Classification Search
CPC .............. A61B 5/0468; A61B 5/04525; A61B 5/04028
See application file for complete search history.

(56) References Cited

U.S. PATENT DOCUMENTS

| 9,295,429 B2 | 3/2016 | Ong et al. | |
| 2004/0068196 A1* | 4/2004 | Massicotte | ........... A61B 5/0006 600/509 |
| 2015/0112182 A1 | 4/2015 | Sharma et al. | |

FOREIGN PATENT DOCUMENTS

WO    2008007236    1/2008

OTHER PUBLICATIONS

International Search Report and Written Opinion; Corresponding PCT Application No. PCT/IB2017/051406 dated Mar. 10, 2017; Authorized Officer Blaine R. Copenheaver; Jun. 6, 2017.

* cited by examiner

*Primary Examiner* — George R Evanisko
(74) *Attorney, Agent, or Firm* — Squire Patton Boggs US LLP

(57) ABSTRACT

A method of detecting abnormal heartbeats includes providing a library of abnormal beat synthesis (ABS) filters, wherein each ABS filter corresponds to a specific cause of a cardiac problem. The method further includes obtaining an ECG of a normal heartbeat of a person and applying an ABS filter from the library of ABS filters to the ECG of the normal heartbeat of the person to generate a potential abnormal ECG. The method further includes monitoring a heartbeat of the person and classifying each heartbeat as either normal or abnormal.

7 Claims, 16 Drawing Sheets

(51) Int. Cl.
*G16H 40/63* (2018.01)
*A61B 5/0402* (2006.01)
*A61B 5/00* (2006.01)
*A61B 5/024* (2006.01)
*A61B 5/0245* (2006.01)
*G06N 3/08* (2006.01)

|      | Truth |    |    |    |    |    |
|------|-------|----|----|----|----|----|
|      |       | N  | S  | V  | F  | Q  |
| Real | N     | N0 | S1 | V1 | F1 | Q1 |
|      | S     | N1 | S0 | V2 | F2 | Q2 |
|      | V     | N2 | S2 | V0 | F3 | Q3 |
|      | F     | N3 | S3 | V3 | F0 | Q4 |
|      | Q     | N4 | S4 | V4 | F4 | Q0 |

Fig. 15

|      | Truth |    |    |
|------|-------|----|----|
|      |       | N  | A  |
| Real | N     | N0 | AX |
|      | A     | NX | A0 |

Fig. 16

|  | | Ground Truth | | | | |
|---|---|---|---|---|---|---|
|  | | N | S | V | F | Q |
| Real | N | 272202 | 6025 | 2643 | 253 | 20 |
|  | S | 866 | 9058 | 11437 | 92 | 0 |
|  | V | 277 | 1923 | 12734 | 60 | 0 |
|  | F | 23 | 17 | 204 | 2 | 0 |
|  | Q | 2 | 7 | 452 | 3 | 0 |

Fig. 17

|  | | Ground Truth | |
|---|---|---|---|
|  | | N | A |
| Real | N | 272202 | 8941 |
|  | A | 1168 | 35989 |

Fig. 18

PERSONALIZED ECG MONITORING FOR EARLY DETECTION OF CARDIAC ABNORMALITIES

FIELD OF INVENTION

The present disclosure relates to a personalized cardiac health monitoring system. More particularly, the present disclosure relates to a cardiac health monitoring system that can be trained by using normal beats of a person.

BACKGROUND

Cardiac health monitoring systems detect tiny electrical changes on the skin that arise from the heart muscle's electrophysiologic pattern of depolarizing during each heartbeat. Prior systems have used patient-specific electrocardiograph ("ECG" or "EKG") classification methods to classify ECG heartbeats. However, such systems can only classify ECG beats after first observing both normal and abnormal beats in the specific patient's ECG record.

For example, FIG. 1A depicts an ECG 100a of a normal heartbeat of a first patient and FIG. 1B depicts an ECG 100b of an abnormal heartbeat of the first patient. Prior personalized classification systems would record both normal and abnormal beats of the first patient, and then employ algorithms to learn the characteristics that are associated with the first patient's abnormal heartbeats. Once sufficient data was acquired, the system could detect future occurrences of abnormal heartbeats in the first patient. However, this technique requires long periods of monitoring to gather sufficient data for the learning algorithm.

Prior attempts have been made to develop a generic classification system that would synthesize potential abnormal ECG data for a new patient based on the observations of other patients. For example, FIG. 2 depicts an ECG 200 of a second patient. ECG 200 happens to depict an abnormal heartbeat. A generic classification system would attempt to determine if the ECG 200 was a normal or abnormal heartbeat based on observations of ECGs of other patients (e.g. ECGs 100a and 100b). However, such generic classification systems are not as accurate as a personalized system.

SUMMARY

In one embodiment, a method of detecting abnormal heartbeats includes providing a library of abnormal beat synthesis (ABS) filters, wherein each ABS filter corresponds to a specific cause of a cardiac problem. The method further includes obtaining an ECG of a normal heartbeat of a person and applying an ABS filter from the library of ABS filters to the ECG of the normal heartbeat of the person to generate a potential abnormal heartbeat. The method further includes ECG monitoring of the person by classifying each heartbeat as either normal or abnormal.

In another embodiment, an abnormal heartbeat detector and alert system includes a sensor configured to contact skin of a user and sense electrical changes on the skin that arise from a heart's electrophysiologic pattern to generate an ECG signal. The system further includes a library of ABS filters, wherein each ABS filter corresponds to a specific cause of a cardiac problem. The system also includes at least one processor configured to monitor the ECG signal, apply at least one ABS filter from the library of ABS filters to the ECG signal of the user to generate a potential abnormal ECG, detect a real abnormal heartbeat, and generate an alert upon detecting the abnormal heartbeat. The system further includes a notification device configured to provide a notification upon receipt of the alert.

In yet another embodiment, a method of detecting abnormal heartbeats includes creating a library of ABS filters by modeling common causes of cardiac problems, including congenital heart defects, coronary artery disease, smoking, high blood pressure, clotting, diabetes, stress, excessive use of alcohol, excessive use of caffeine, and drug use in a signal domain as degradation of normal beats to abnormal beats, and modeling each normal-to-abnormal beat degradation by a linear and time-invariant filter kernel using a benchmark dataset of ECG records. The method further includes generating an ECG signal from a normal heartbeat of a person, applying an ABS filter from the library of ABS filters to the ECG signal of the normal heartbeat of the person to generate potential abnormal heartbeats into a personal ECG dataset of the person. Finally, 1D Convolutional Neural Network (CNN) is trained over the personalized dataset and will be used in the monitoring device to classify each (real) heartbeat of the person as either normal or abnormal. If an abnormal beat is detected, an alert as a sound or light will be triggered to warn the person.

BRIEF DESCRIPTION OF DRAWINGS

In the accompanying drawings, structures are illustrated that, together with the detailed description provided below, describe exemplary embodiments of the claimed invention. Like elements are identified with the same reference numerals. It should be understood that elements shown as a single component may be replaced with multiple components, and elements shown as multiple components may be replaced with a single component. The drawings are not to scale and the proportion of certain elements may be exaggerated for the purpose of illustration.

FIG. 15 shows a parameterized, cumulated confusion matrix, where the ground-truth numbers are in the columns;

FIG. 16 shows the deducted confusion matrix;

FIG. 17 shows the confusion matrix cumulated by the classification results of 10 Convolutional Neural Networks for some patients in the test partition of the MIT-BIH benchmark ECG database; and FIG. 18 shows the 2×2 confusion matrix deducted from the matrix in FIG. 17.

DETAILED DESCRIPTION

A system and method for detecting abnormal heartbeats is described herein. The system and method rely on an abnormal beat syntheses approach, which can create potential abnormal beats for an individual by using the library of filters over her regular normal beat. To design such filters, common causes of cardiac problems such as congenital heart defects, coronary artery disease, smoking, high blood pressure, clotting, diabetes, stress, excessive use of alcohol, excessive use of caffeine, and drug use, are modeled in the signal domain as the degradation of normal beats to abnormal beats. Using a benchmark dataset of ECG records, each normal-to-abnormal beat degradation will be modeled by a linear and time-invariant ("LTI") filter kernel.

Figure 1A:
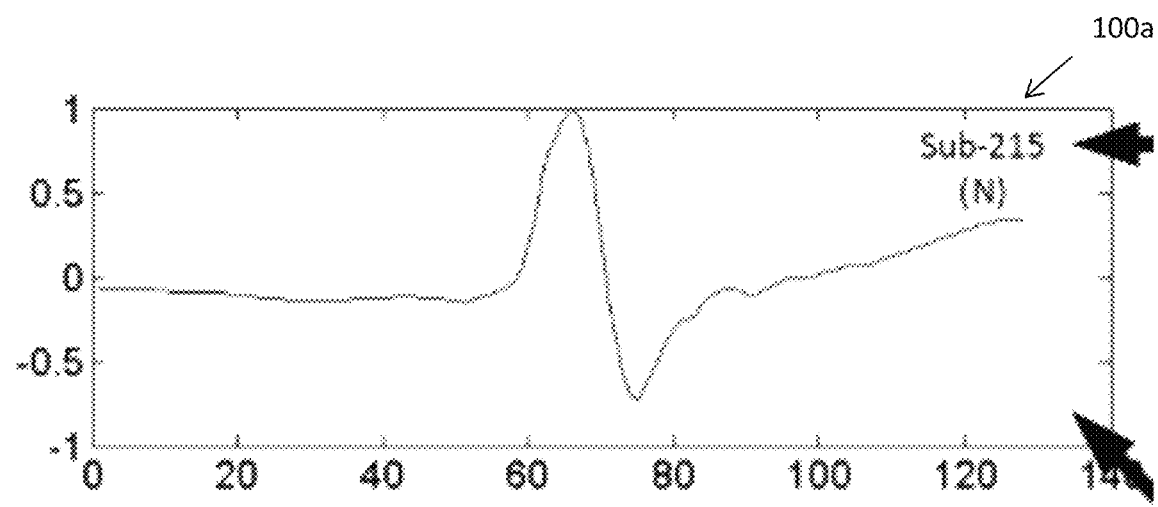
FIG. 1A illustrates an ECG of a normal heartbeat of a first patient.
Figure 1B:
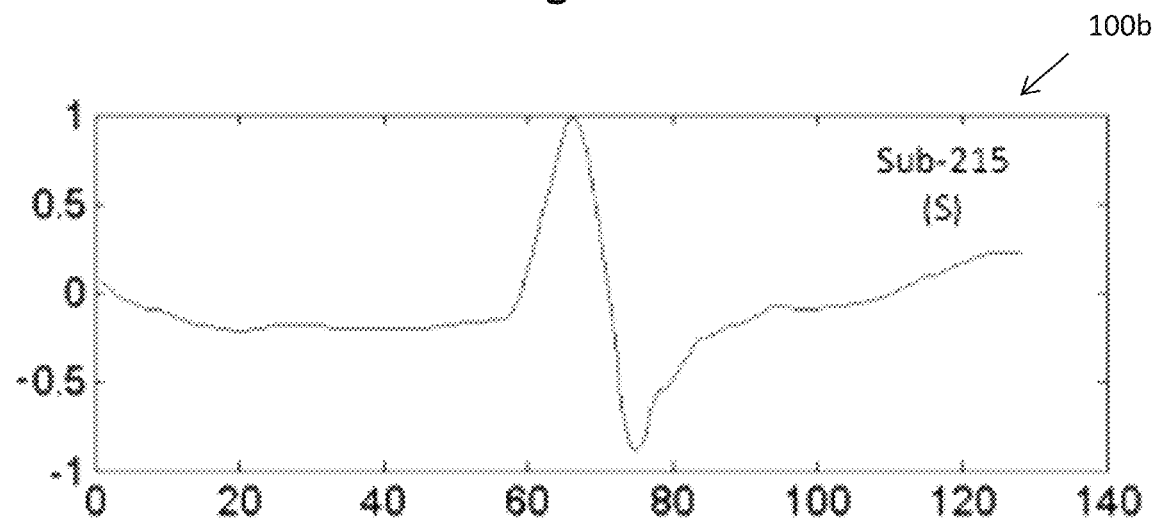
FIG. 1B illustrates an ECG of an abnormal heartbeat of the first patient.
Figure 2:
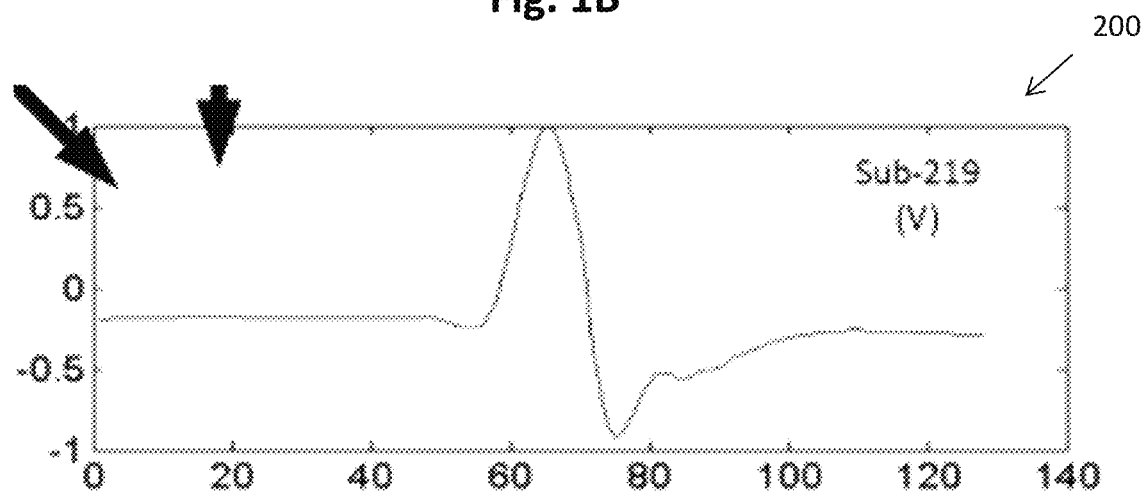
FIG. 2 illustrates an ECG of an abnormal heartbeat of a second patient.
Figure 3:
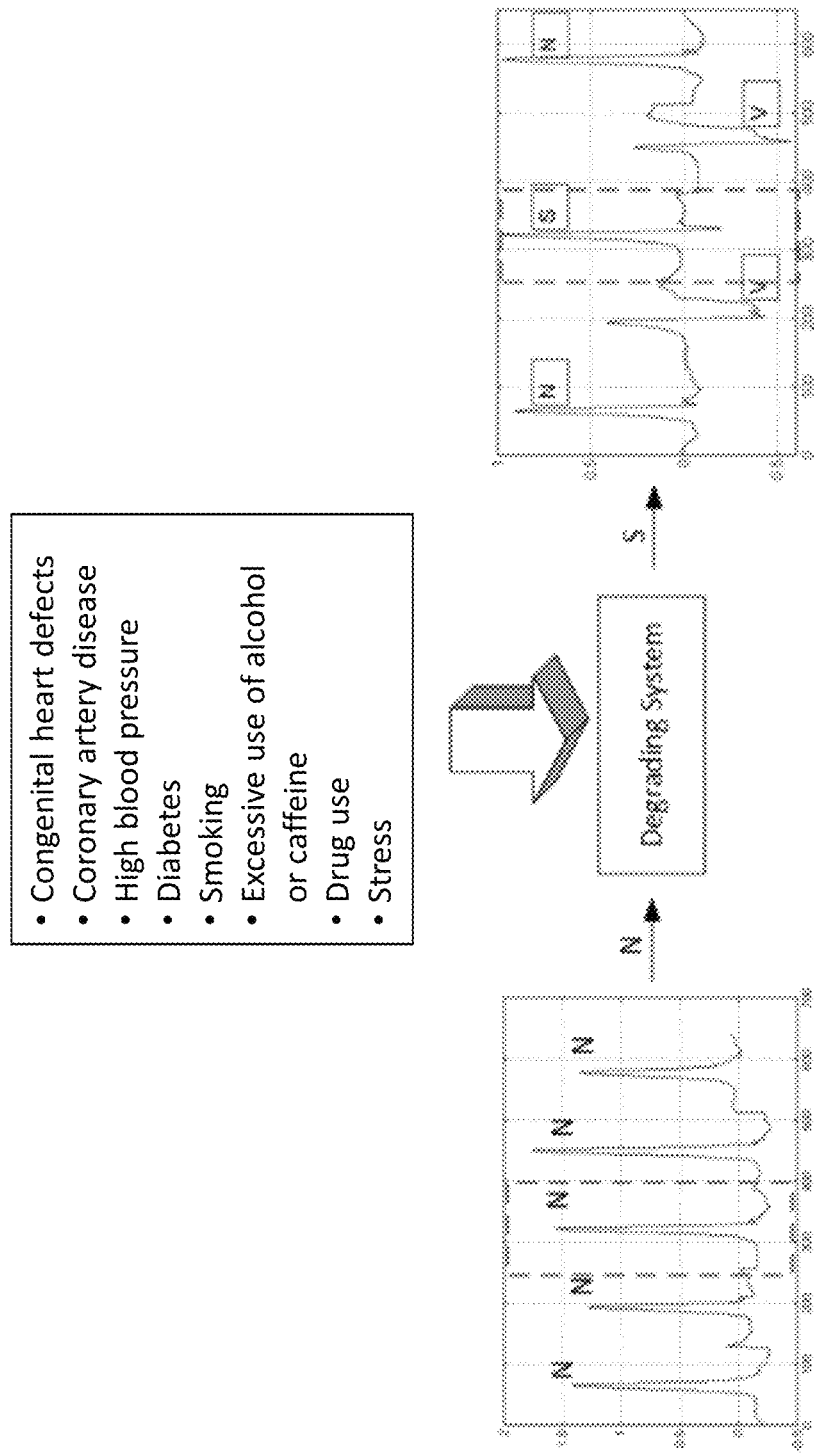
FIG. 3 is a schematic drawing illustrating common causes of degradation of the heart of a particular patient being modeled in a dataset as a "degrading system" that turns regular normal beats to abnormal beats.

In this way, the common causes of degradation of the heart of a particular patient are modeled in the dataset as a "degrading system" that turns regular normal beats to abnormal beats as shown in FIG. 3. If the same physical cause that occurs on the person being monitored, then the same degrading system will able to synthesize similar abnormal beats that will occur. Using the library of filters over a regular normal beat generates a set of potential abnormal ECG beats of a person. A dedicated classifier can thus be trained in advance so as to be used as an early detection system for ECG abnormalities.

Figure 4:
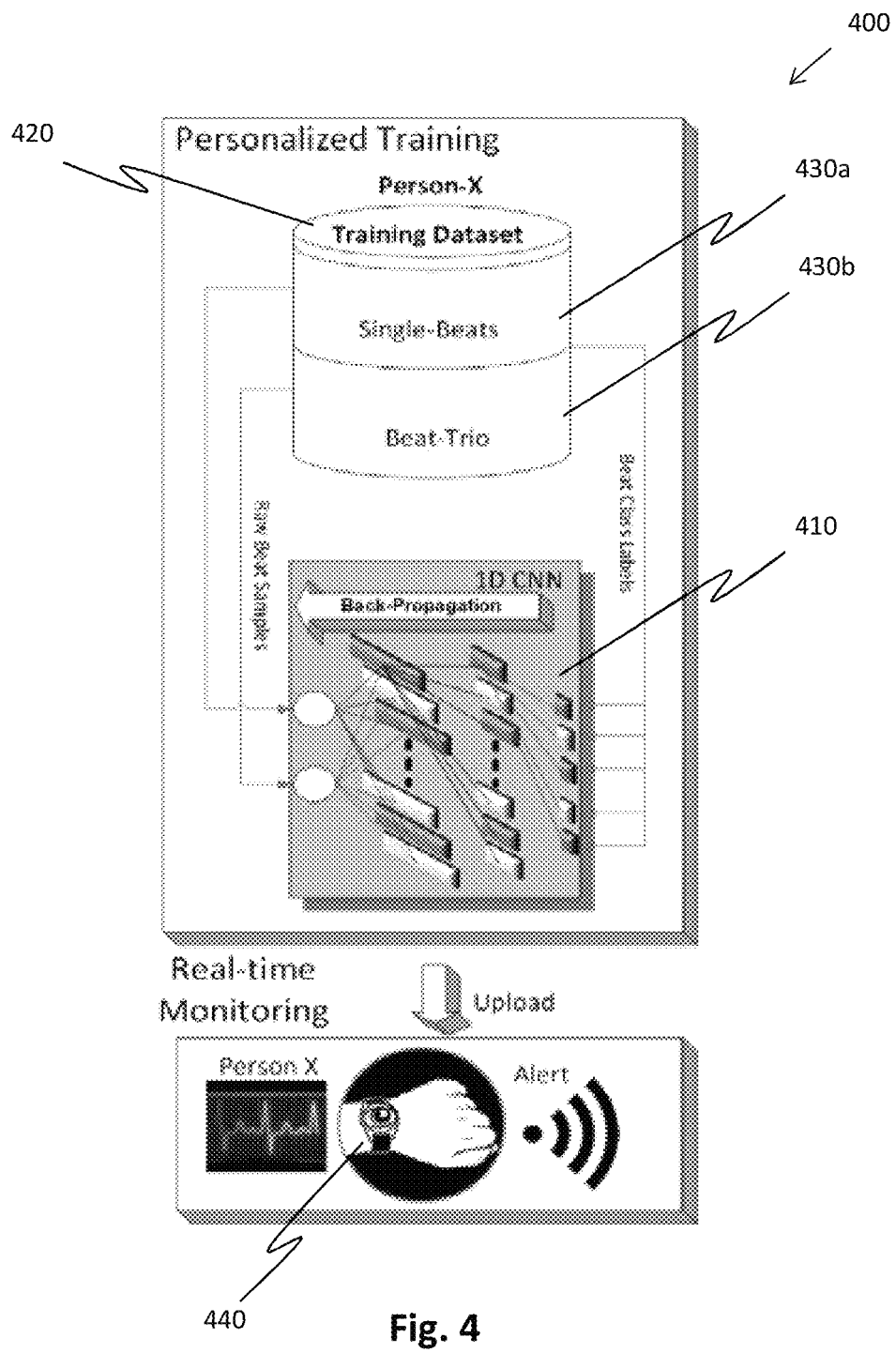
FIG. 4 is a schematic drawing illustrating a personalized ECG monitoring system.

FIG. 4 is a schematic drawing depicting a personalized ECG monitoring system 400. The system 400 employs an adaptive implementation of 1D Convolutional Neural Networks (CNNs) 410 that fuses feature extraction and classification of ECG classification into a single learning body. During the training, each block is optimized by the Back-Propagation technique to maximize the classification performance.

The system 400 requires: (1) creation of the abnormal beat syntheses (ABS) filter library by performing least-squares (LS) system identification, (2) creation of the personalized training dataset 420 by the syntheses of potential abnormal beats using the ABS filter library over the person's average normal beat, and (3) training a dedicated 1D CNN 410 for that person over her training dataset 420. The training dataset 420 includes both single beat representation 430a and beat-trios 430b, as will be described in more detail below.

Since the proposed solution is intended for monitoring healthy individuals, no real abnormal beats will be used in the personal training dataset. In other words, the training dataset of each individual 1D CNN encapsulates only the real normal (N) beats of the person. Once trained with the real normal and synthesized abnormal beats, the final classifier will then be uploaded to the ECG monitor of the person for real-time health monitoring. The overall workflow of the proposed solution is illustrated on a possible client/server architecture in FIG. 5.

Once the 1D CNN 410 is trained it can then be used to classify each beat in real-time and hence it can detect abnormal beats at the moment they occur. Simple 1D CNNs are easier to train with only few dozens of back-propagation (BP) iterations and can thus perform the classification task at high speed (requiring only few hundreds of 1D convolutions). This makes them a suitable for real-time ECG monitoring and early detection of hearth arrhythmia on light-weight devices, such as a smart watch 440 or a dedicated heartbeat monitor that can be worn with a wrist band or chest strap.

Figure 5:
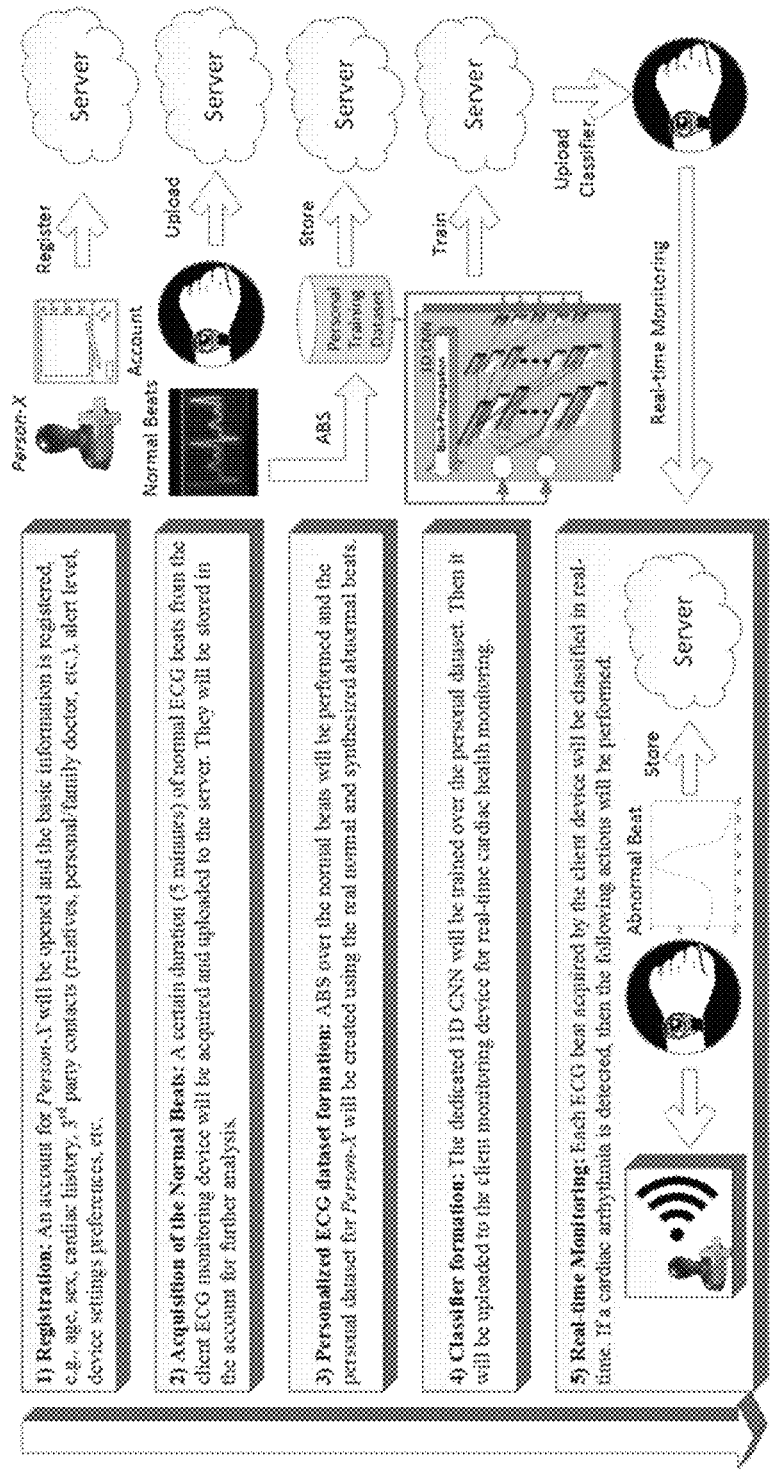
FIG. 5 is a schematic drawing illustrating a workflow of real-time monitoring for cardiac arrhythmia on a potential client/server architecture.

The device 440 includes at least one sensor (not shown) configured to contact the skin of a user and sense electrical changes that arise from a heart's electrophysiologic pattern to generate an ECG signal. As illustrated in FIG. 5, the device 440 relies on a personalized classifier that is downloaded from a serving computer (i.e., the server). The personalized classifier is trained in the server over the personal dataset created for the person. To synthesize the abnormal beats in the personal dataset, ABS operation is first performed also in the server, wherein each ABS filter corresponds to a specific cause of a cardiac problem. The device 440 further includes at least one processor configured monitor the ECG signal, compare the ECG signal to the potential abnormal ECG, and generate an alert upon the 1D CNN classifying the ECG as an abnormal (or potentially abnormal) ECG. The device further includes a notification device configured to provide a notification upon receipt of the alert. In the illustrated embodiment, the notification device is a speaker that issues an alert, such as a beep or an alarm. In alternative embodiments, the notification device may be a display screen, an indicator light, a vibrating device, a printer, or a radio frequency transmitter.

Figure 6:
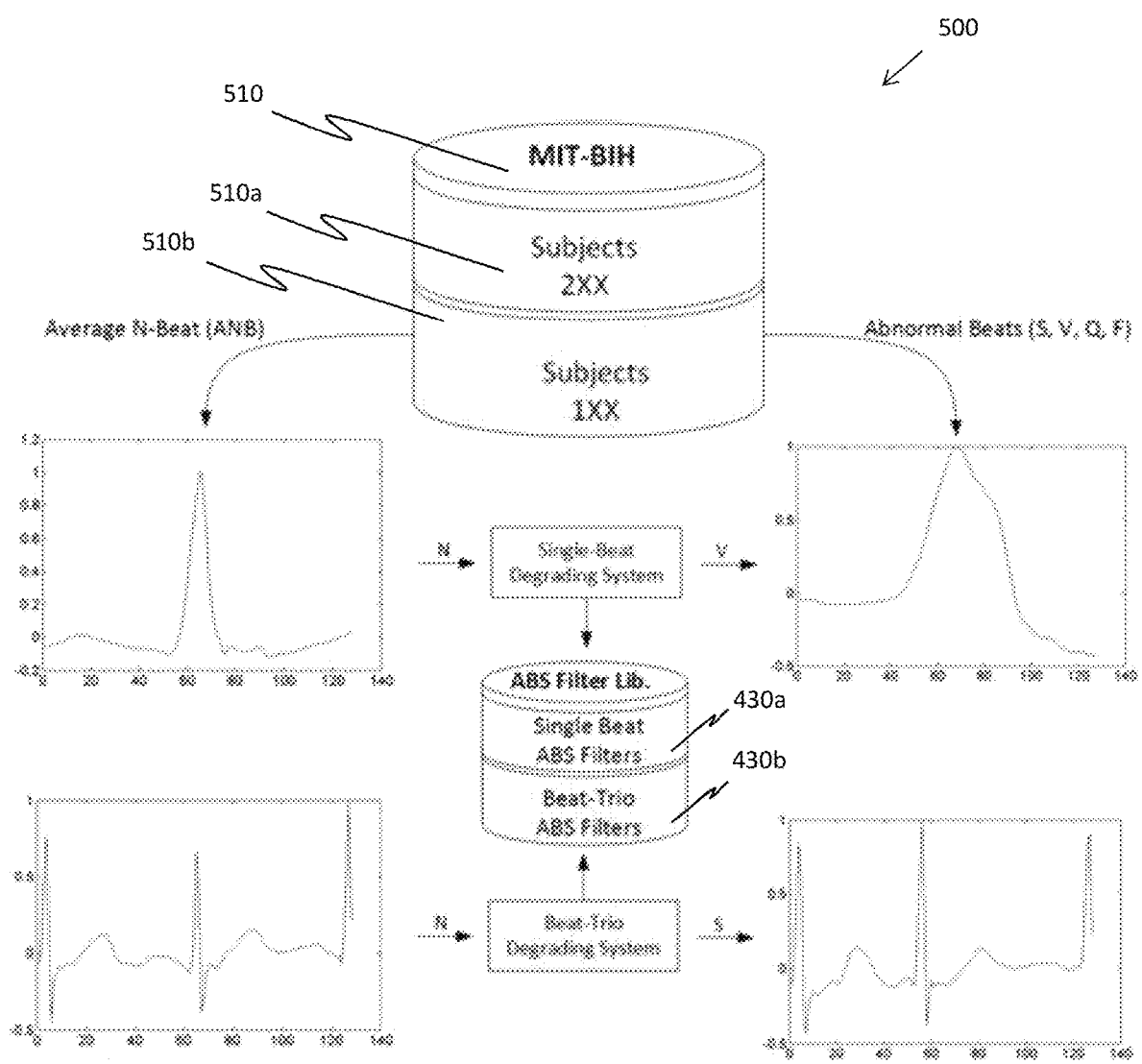
FIG. 6 is a schematic drawing illustrating a process of designing abnormal beat syntheses filters.

FIG. 6 is a schematic drawing illustrating a process of designing ABS filters. The process will be described with reference to FIGS. 4-6. In the illustrated embodiment, a benchmark arrhythmia database maintained by the Massachusetts Institute of Technology and Beth Israel Hospital (known as the MIT/BIH Arrhythmia Database) 510 is employed. In alternative embodiments, other previously existing database may be used for the creation of the ABS filter library and performance evaluation of the personalized abnormal beat detection. In another alternative embodiment, a new database may be created.

In one embodiment, the MIT/BIH Arrhythmia Database 510 contains 48 records, each containing two-channel ECG signals for 30-minute duration selected from 24-hour recordings of 47 individuals. Continuous ECG signals are band-pass filtered at 0.1-100 Hz and then digitized at 360 Hz. The database contains annotation for both timing information and beat class information verified by independent experts.

In one particular embodiment, 44 records from the MIT/BIH Arrhythmia Database were used, excluding 4 records which contain paced heartbeats. The first 20 records, which include representative samples of routine clinical recordings, were used to select certain number of representative beats to be included in the common training data. Therefore, these records were used as the training partition of the database. The remaining 24 records contain uncommon but clinically significant arrhythmias such as ventricular, junctional, and supraventricular arrhythmias. These records may be used as the testing partition of the database.

ECG beats may be classified into five heartbeat types: N (beats originating in the sinus mode), S (supraventricular ectopic beats), V (ventricular ectopic beats), F (fusion beats), and Q (unclassifiable beats). The raw data of each beat is represented by 128 samples by down-sampling. There are two distinct beat representations: in the single beat representation 430a, equal number of samples from each side from the R (center) point of the beat are used. To learn the temporal characteristics of each beat, a beat-trio 430b is formed from its neighbor beats. Therefore, the difference in timing information of the center beat together with its neighbors in the beat-trio formation 430b can indicate timing information related ECG anomalies such as the presence of an APC (S) beat.

An abnormal beat syntheses (ABS) filter models the degradation of a regular normal beat to an abnormal beat. This degradation represents a cause of the cardiac arrhythmia that physically degrades a healthy heart (with an output of a regular normal beat) to an unhealthy one that outputs abnormal beats. If ABS filters are assumed to be linear and time-invariant (LTI), the input-output expression can be written as:

$$b[n] = h[n] \times a[n] = \text{IDFT}(H(f) \cdot A(f))$$

$$a[n]: a[0], a[1], a[N-1]$$

$$b[n]: b[0], b[1], b[N-1]$$

$$h[n]: h[0], h[1], h[N-1] \quad (1)$$

where a and b are N-length input and output signals corresponding to (regular) normal and abnormal beats, respectively, and h is the M-length filter coefficients of the LTI system. H(f) and B(f) are the DFT of h and b, respectively.

One can derive h from the IDFT of the ratio between the DFTs of b and a, as follows:

$$h[n] = IDFT\left(\frac{B(f)}{A(f)}\right) \quad (2)$$

where B(f) is the DFT of the output signal b. However, the singularities and low values of A(f) due to noise will make it infeasible to compute the h accurately. Instead we shall derive it from the Least-Squares (LS) optimization directly. One can write the linear convolution as:

$$b[n] = h[n] * a[n] = \sum_{m=0}^{M-1} a[n-m]h[m] \quad (M \leq N) \quad (3)$$

The convolution output will have the length, $N+M-1$ where only the first N samples are considered, because the output signal (abnormal beat) has the same length as the input. This can be written in matrix equation as follows:

$$\begin{bmatrix} a[0] & 0 & 0 & 0 & \ldots & 0 \\ a[1] & a[0] & 0 & 0 & \ldots & 0 \\ a[2] & a[1] & a[0] & 0 & \ldots & 0 \\ \ldots & \ldots & \ldots & \ldots & \ldots & \ldots \\ a[N-1] & a[N-2] & a[N-3] & \ldots & \ldots & a[N-M] \end{bmatrix} \begin{bmatrix} h[0] \\ h[1] \\ \ldots \\ h[M-1] \end{bmatrix} = \quad (4)$$

$$\begin{bmatrix} b[0] \\ b[1] \\ \ldots \\ \ldots \\ b[N-1] \end{bmatrix}$$

or equivalently in a linear system equation:

$$Ax = b \quad (5)$$

where A is the N×M matrix with the shifted input signal samples, x is the column vector of filter coefficients, $(x(i) = h[i])$ and b is the column vector of output signal, b. The LS solution of this equation, $x_{LS}$, can be expressed as follows:

$$x_{LS} = \min_{x \in R^M} \|b - Ax\|^2 = (A^T A)^{-1} A^T b \quad (6)$$

However, the matrix, A can be rank deficit, i.e., rank(A)= r<M. In this case, the matrix $A^T A$ will be singular and inverse cannot be taken. To address this, we can write the Singular Value Decomposition (SVD) of A as:

$$A = U \Sigma V^T = \sum_{i=1}^{r} \sigma_i u_i v_i^T \quad (7)$$

where U and V are N×N and M×M orthogonal matrices which holds the eigen-vectors of the square matrices, $AA^T$ and $A^T A$, respectively, as the column vectors.

The N×M matrix, $\Sigma$, can be expressed as:

$$\Sigma = \begin{bmatrix} \sigma_1 & 0 & 0 & \ldots & 0 & 0 & \ldots & 0 \\ 0 & \sigma_2 & 0 & \ldots & 0 & 0 & \ldots & 0 \\ 0 & 0 & \sigma_3 & \ldots & 0 & 0 & \ldots & 0 \\ \ldots & \ldots & \ldots & \ldots & \ldots & \ldots & \ldots & 0 \\ 0 & 0 & 0 & \ldots & \sigma_r & 0 & \ldots & 0 \\ 0 & 0 & 0 & \ldots & 0 & 0 & \ldots & 0 \\ \ldots & \ldots & \ldots & \ldots & \ldots & \ldots & \ldots & \ldots \\ 0 & 0 & 0 & 0 & 0 & 0 & \ldots & 0 \end{bmatrix} \quad (8)$$

where $\sigma_1 > \sigma_2 > \sigma_r$ are the singular values or equivalently the eigen-values of the matrices, $A^T A$ and $AA^T$.

This can yield the LS solution, $x_{LS}$, regardless from the singularity of A as:

$$x_{LS} = V \Sigma^{-1} U^T b = \sum_{i=1}^{r} \frac{1}{\sigma_i} v_i u_i^T b \quad (9)$$

However, the LS solution, $x_{LS}$, can still yield to very large values, the so-called "explosion" of the LS solution, due to the noisy values in matrix A (the input) or in vector b (the output), or both since they, the ECG data in general, are indeed susceptible to noise. A crucial disadvantage therein is that the smaller non-zero singular values will result in even larger the explosion of $x_{LS}$. To prevent this, the LS solution may be regularized by optimizing the LS error together with the magnitude of the LS solution as:

$$x_{RLS} = \min_{x \in R^M} (\|b - Ax\|^2 + \lambda^2 \|x\|^2) \qquad (10)$$

where $\lambda$ is the regularization parameter. This joint optimization may be expressed as:

$$x_{RLS} = \min_{x \in R^M} \left\| \begin{pmatrix} b \\ 0 \end{pmatrix} - \begin{pmatrix} A \\ \lambda I \end{pmatrix} x \right\|^2 = \min_{x \in R^M} \|b_\lambda - A_\lambda x\|^2 \qquad (11)$$

where $A_\lambda$ is now Mx(M+N) a full-rank matrix (r=M) and therefore, the LS solution over $A_\lambda$ can be obtained by using Eq. (6) as:

$$x_{LS}(\lambda) = \min_{x \in R^M} \|b_\lambda - A_\lambda x\|^2 = (A_\lambda^T A_\lambda)^{-1} A_\lambda^T b_\lambda \qquad (12)$$

$$= (A^T A + \lambda^2 I)^{-1} A^T b$$

The $i^{th}$ eigen-vector of $(A_\lambda^T A_\lambda)$ can be obtained by:

$$A_\lambda^T A_\lambda v_i = (A^T A + \lambda^2 I) v_i = (\sigma_i^2 + \lambda^2) v_i \qquad (13)$$

The matrix $A_\lambda^T A_\lambda$ has the same eigen-vector, $v_i$, as the matrix $A^T A$ but a larger eigen-value $(\sigma_i^2 + \lambda^2)$. Therefore, using the orthogonality of the eigen-vectors, the eigen-vector decomposition of $A_\lambda^T A_\lambda$, and its inverse is:

$$A_\lambda^T A_\lambda = \sum_{j=1}^M (\sigma_j^2 + \lambda^2) v_j v_j^T = V \Lambda V^T \qquad (14)$$

$$(A_\lambda^T A_\lambda)^{-1} = \sum_{j=1}^M \frac{1}{(\sigma_j^2 + \lambda^2)} v_j v_j^T = V \Lambda^{-1} V^T$$

Using Equations (7) and (9) yields the regularized LS solution, $x_{RLS}$, expressed as:

$$x_{RLS} = x_{LS}(\lambda) = (A_\lambda^T A_\lambda)^{-1} A^T b \qquad (15)$$

$$= \left( \sum_{j=1}^M \frac{1}{\sigma_j^2 + \lambda^2} v_j v_j^T \right) \left( \sum_{i=1}^r \sigma_i v_i u_i^T \right) b$$

$$= \left( \sum_{j=1}^T \frac{\sigma_j}{\sigma_j^2 + \lambda^2} v_j u_j^T b \right)$$

Comparing regularized LS solution in Eq. (15) with the LS solution in Eq. (9), the effects of those noise-like singular values over the solution can be suppressed with a practical choice of $\lambda$. For example, $\lambda$ may be selected to be between 0.1 and 0.5. As a result, Equation (15) may be used to design an ABS filter for each pair of normal-abnormal ECG beats and as illustrated in FIG. 6. A library of ABS filters can be designed for each representation of a single-beat 430a and beat-trio 430b.

In one embodiment, ABS filters are designed using the first 5 minutes of data plus the common training data selected among the records in training partition (subjects with IDs 1XX) 510a of the MIT/BIH arrhythmia database 510. First the average normal beat (ANB) is selected among the N beats in the first 5 minutes. ANB will be the sole input, a, of the ABS filters created from that subject. Then for each abnormal beat of the subject an M-length ABS filter is designed.

Two filter selection models can be applied in order to eliminate similar and all-pass (impulsive) filters. The former occurs if the abnormal beats of the subject are similar with each other. In that case one or few representative filters will suffice to model abnormal beat syntheses from that patient. The latter occurs when the abnormal beat is similar to the ANB. Especially for single beat representation some S-beats can have the same pattern as an N-beat. Those "all-pass" filters can be left out. Both selections are performed by evaluating the mean-normalized variance of the filter coefficients. Those filters, which yield the highest variances will be selected into the ABS filter library.

Either filter selection is optional for the patient-specific part (first 5 minutes) since one can also use the entire data from this part. Additionally, the common data part may be limited to a certain number of beats (e.g., 245) within the rest of the record (excluding the first 5 minutes).

Once formed, for each beat representation, the ABS filter library will then be used to synthesize the abnormal beats of each patient in the test partition (subjects with IDs 2XX) 510b. In this embodiment, no real abnormal beat will be used in the training dataset of the CNN. In other words, the training dataset of a 1D CNN encapsulates only the real normal (N) beats of the subject in the test partition which are taken only within the first 5 minutes of the record. Once trained with the real normal and synthesized abnormal beats, the abnormal beat detection performance of the CNN will then be evaluated over the real abnormal beats of the subject.

Figure 8:
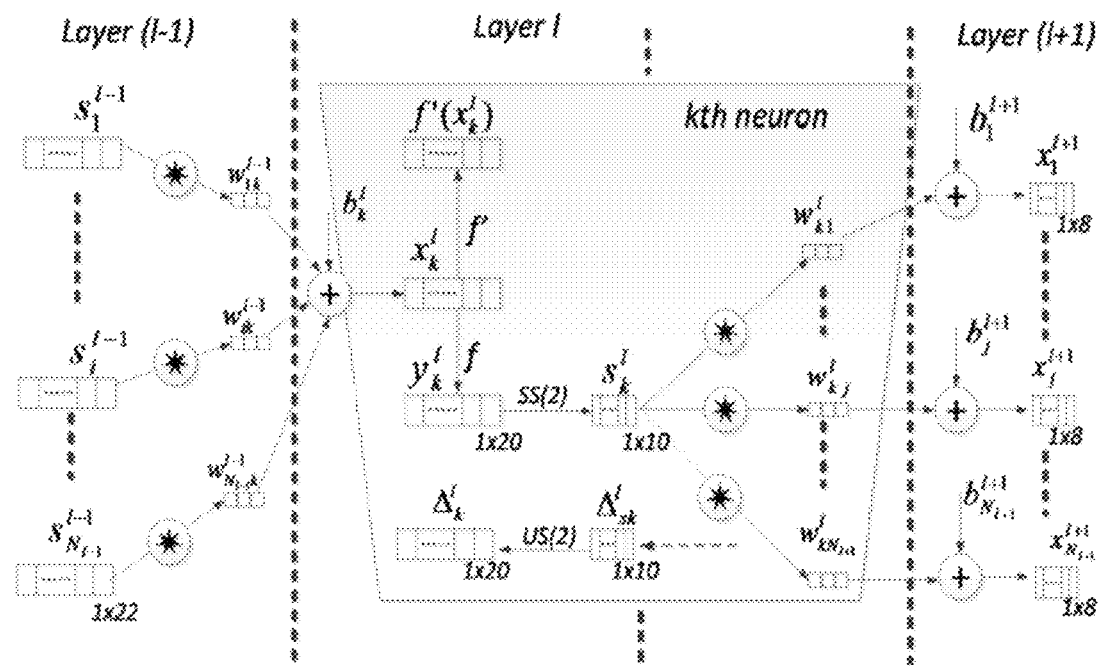
FIG. 8 is a schematic drawing illustrating an adaptive 1-D Convolutional Neural Network configuration.

FIG. 8 illustrates an adaptive CNN configuration 700. There are two types of layers in the adaptive 1D CNNs: 1) CNN-layers where both 1D convolutions and sub-sampling occur, and 2) MLP-layers that are identical to the hidden and output layers of a standard MLP. The CNN-layers process the raw data and learn to extract such features that can be used by the classification performed by the MLP-layers. Therefore, both feature extraction and classification operations are fused into one body that can be optimized to maximize the classification performance. CNNs can also provide a low computational complexity.

In the CNN-layers, the 1D forward propagation (FP) can be expressed as:

$$x_k^l = b_k^l + \sum_{i=1}^{N_{l-1}} conv1D(w_{ik}^{l-1}, s_i^{l-1}) \qquad (16)$$

where $x_k^l$ is the input, $b_k^l$ is the bias of the $k^{th}$ neuron at layer l, and $s_i^{l-1}$ is the output of the $i^{th}$ neuron at layer l–1. $w_{ik}^{l-1}$ is the kernel from the $i^{th}$ neuron at layer l–1 to the $k^{th}$ neuron at layer l.

With such an adaptive design, the number of hidden CNN layers can be set to any practical number because the sub-sampling factor of the output CNN layer (the hidden CNN layer just before the first MLP layer) is set to the dimensions of its input map. For example, if the layer l+1 would be the output CNN layer, then the sub-sampling factors for that layer is automatically set to ss=8 because the input map dimension is 8 in this sample illustration. The dimension of the input maps will gradually decrease due to the convolution without zero padding. For example, as shown in FIG. 8, the dimension of the neuron output is 22 at the layer l−1 that is reduced to 20 at the layer l. As a result, the dimension of the input maps of the current layer is reduced by K−1 where K is the size of the kernel.

EXPERIMENTAL RESULTS

In one study, each ECG beat was represented by 128 samples in two different configurations: single-beat and beat-trio. For single-beat representations, the samples were centered around the R-peak. For a beat-trio they were obtained by down-sampling the sequence between the previous and the following R-peaks. A simple 1D CNN was used in all experiments, with 4 CNN layers and 2 MLP layers. The 1D CNN used in all experiments had 32, 16 and 16 neurons on the 1st, 2nd and 3rd hidden CNN layers and 32 neurons on the hidden MLP layer. The output (MLP) layer size was 5 and the input (CNN) layer size was 2. The kernel size of the CNN was 7 and the sub-sampling factor was 3. The sub-sampling factor for the last CNN-layer was automatically set to 5.

In these experiments, the maximum number of BP iterations was set to 50. Additionally, the minimum train classification error level that was set to 8% to prevent over-fitting. Therefore, the training would terminate if either of the criteria was met. The learning factor, $\varepsilon$, was initially set as 0.001. A global adaptation was applied during each BP iteration: if the training mean squared error (MSE) decreased in the iteration, $\varepsilon$ was increased by 5%. Otherwise, $\varepsilon$ was reduced by 30% for the next iteration. Ten individual BP runs were performed for each subject in the database. Two detection performance metrics—average abnormal beat detection accuracy and false alarm rate—were reported.

Figure 9A:
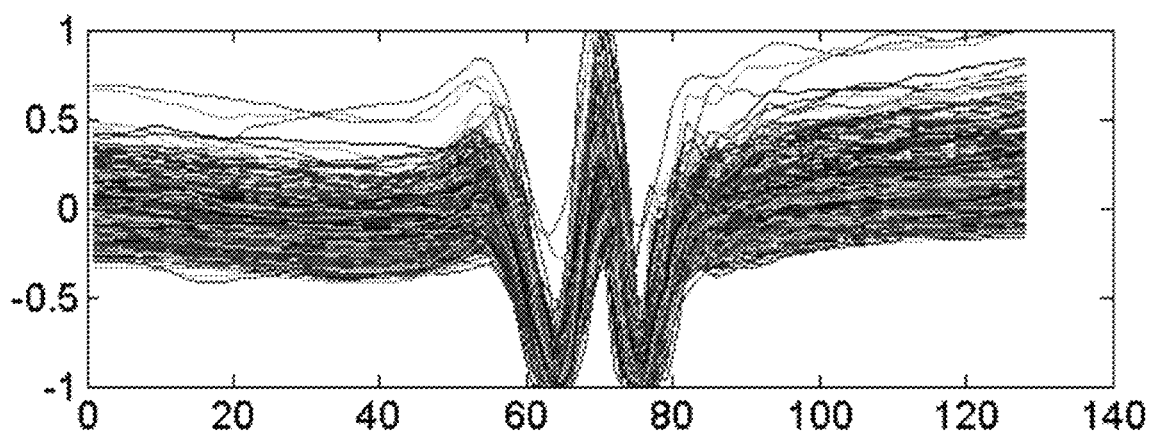
FIGS. 9A-D are schematic drawings illustrating two typical average normal beat selections for two subjects.
Figure 9B:
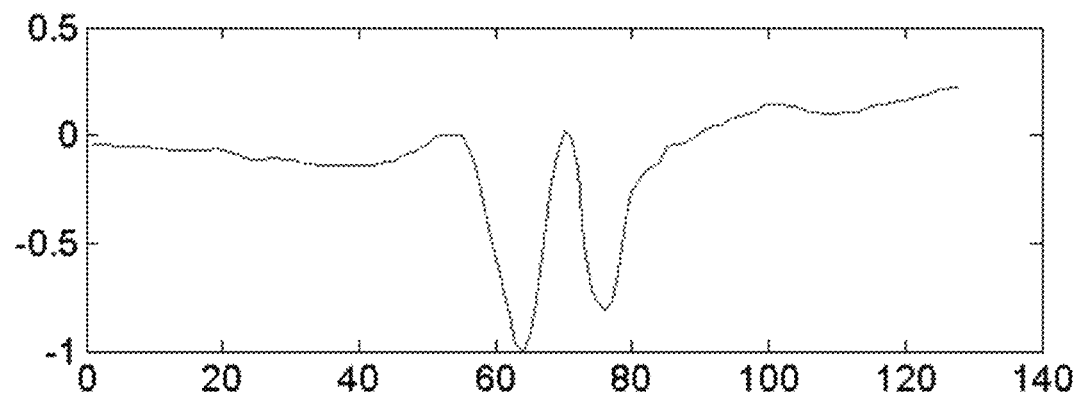
Figure 9C:
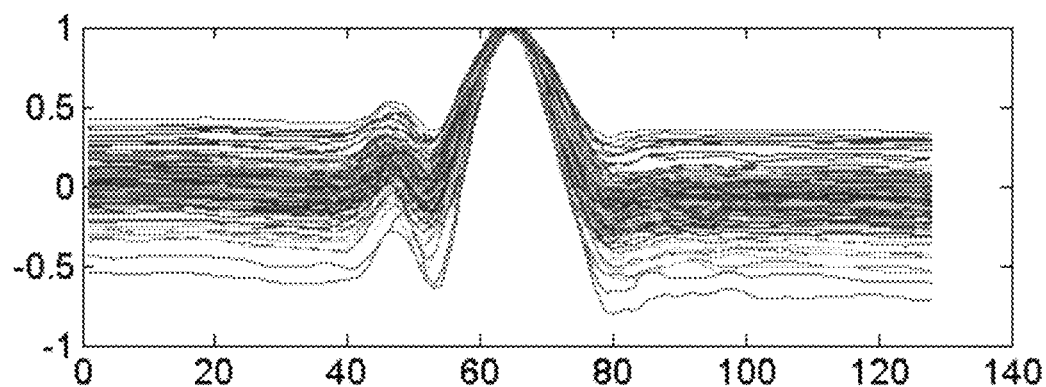
Figure 9D:
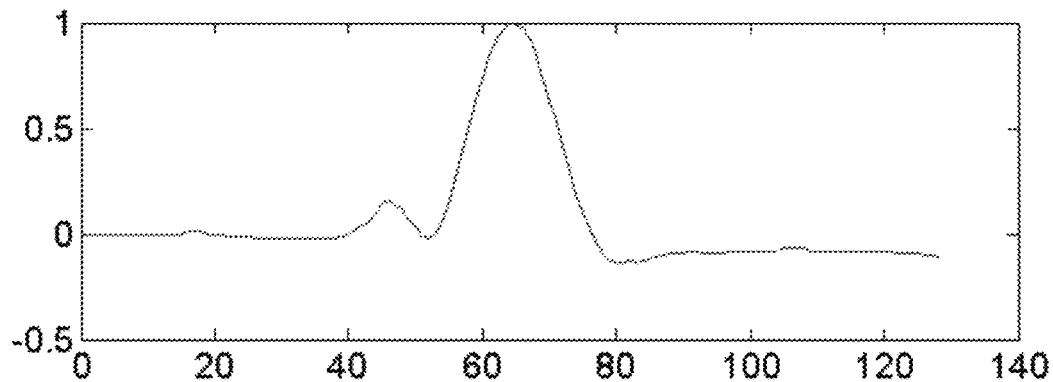

To evaluate the Abnormal Beat Syntheses (ABS) approach, first average of the normal beats was computed using only the first 5 minutes of the record for both single beat and beat-trio representations. The N-beat that was closest to the average was selected as the average normal beat (ANB). FIGS. 9A-D show two typical ANB selections for the two subjects. More specifically, FIGS. 9A and 9B show a beat-trio and a single beat, respectively, for a first subject and FIGS. 9C and 9D show a beat-trio and a single beat, respectively, for a second subject.

Over the training partition of the database, 464 filters were created in the ABS filter library and were used to synthesize abnormal beats for the subjects in the test partition. The value of $\lambda$ was set at 0.1 and the minimum variances for filter selection were set at 0.1 and 0.15 for the S and V type abnormalities, respectively. There was no selection for Q and F type anomalies—all ABS filters for Q and F type abnormal beats were kept in the library.

Figure 10A:
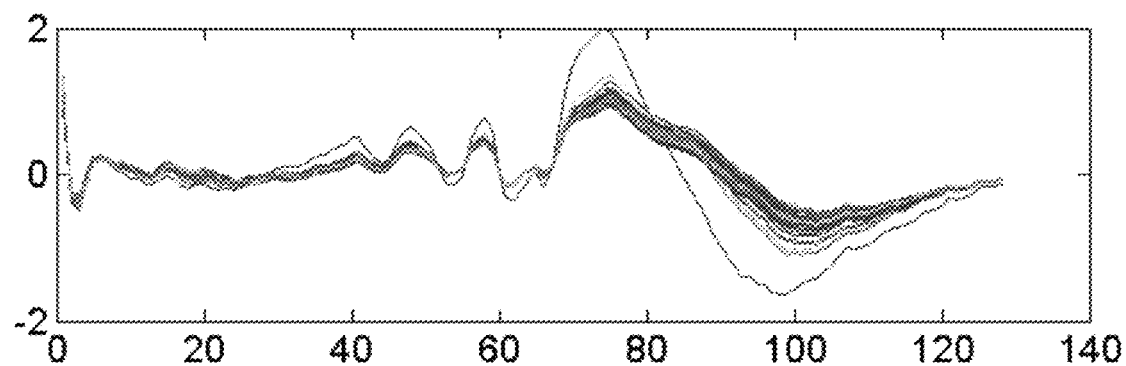
FIGS. 10A-D are schematic drawings illustrating abnormal beat syntheses filters formed for the V beats from the patient-specific training data of a third subject and fourth subject and the few selected abnormal beat syntheses filters among all abnormal beat syntheses filters based on the variance.
Figure 10B:
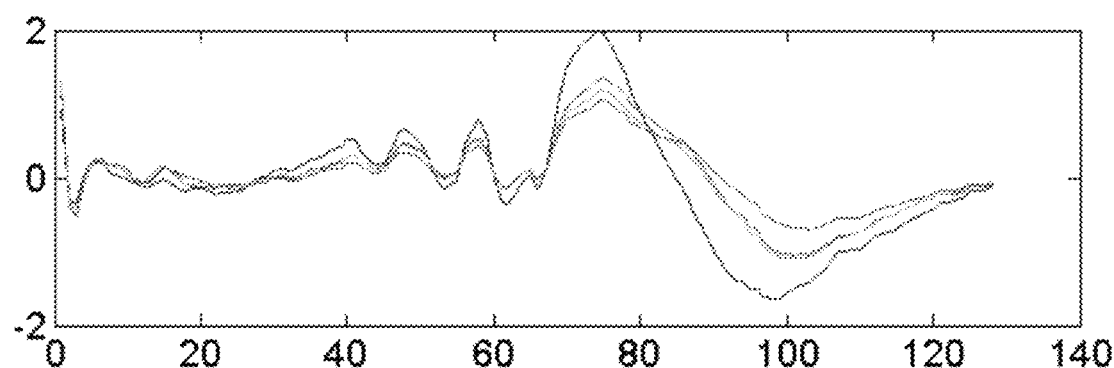
Figure 10C:
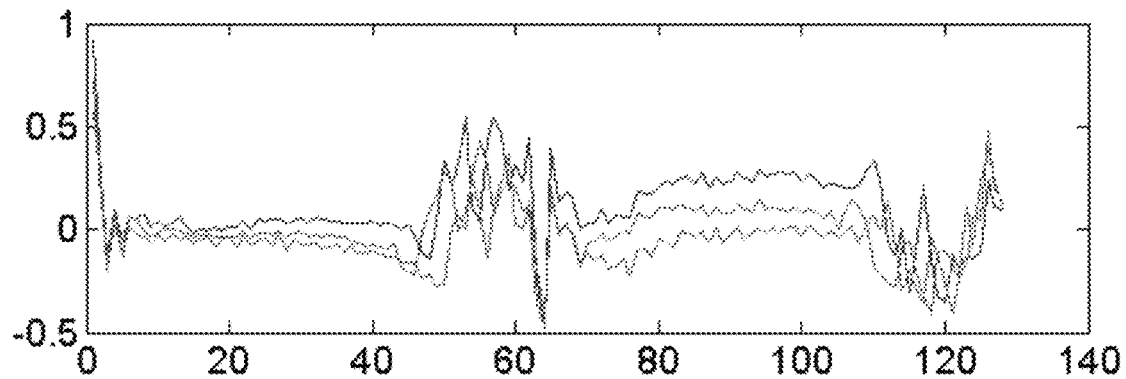
Figure 10D:
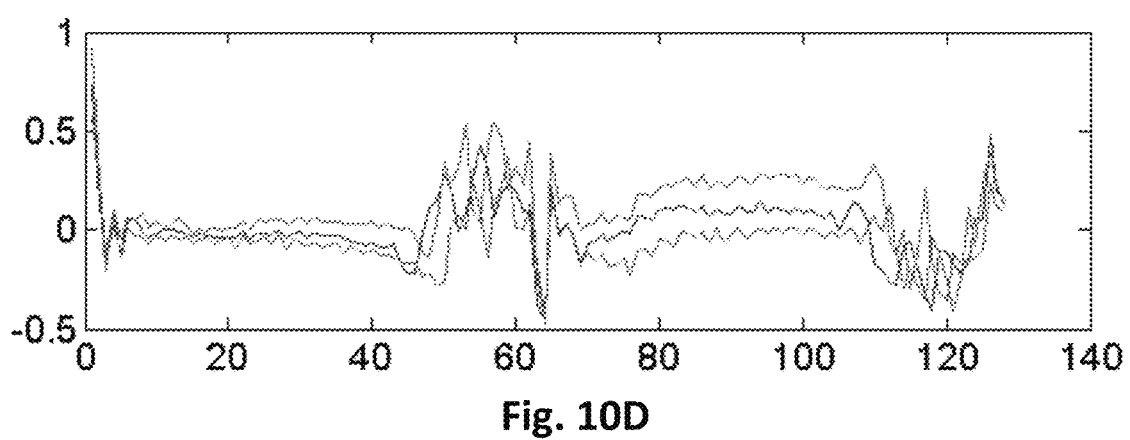

FIGS. 10A-D show the ABS filters formed for the V beats from the patient-specific training data of a third subject and fourth subject. Specifically, FIGS. 10A and 10B show the total and selected ABS filters, respectively, for the third subject. FIGS. 10C and 10D show the total and selected ABS filters, respectively, for the fourth subject.

Figure 7:
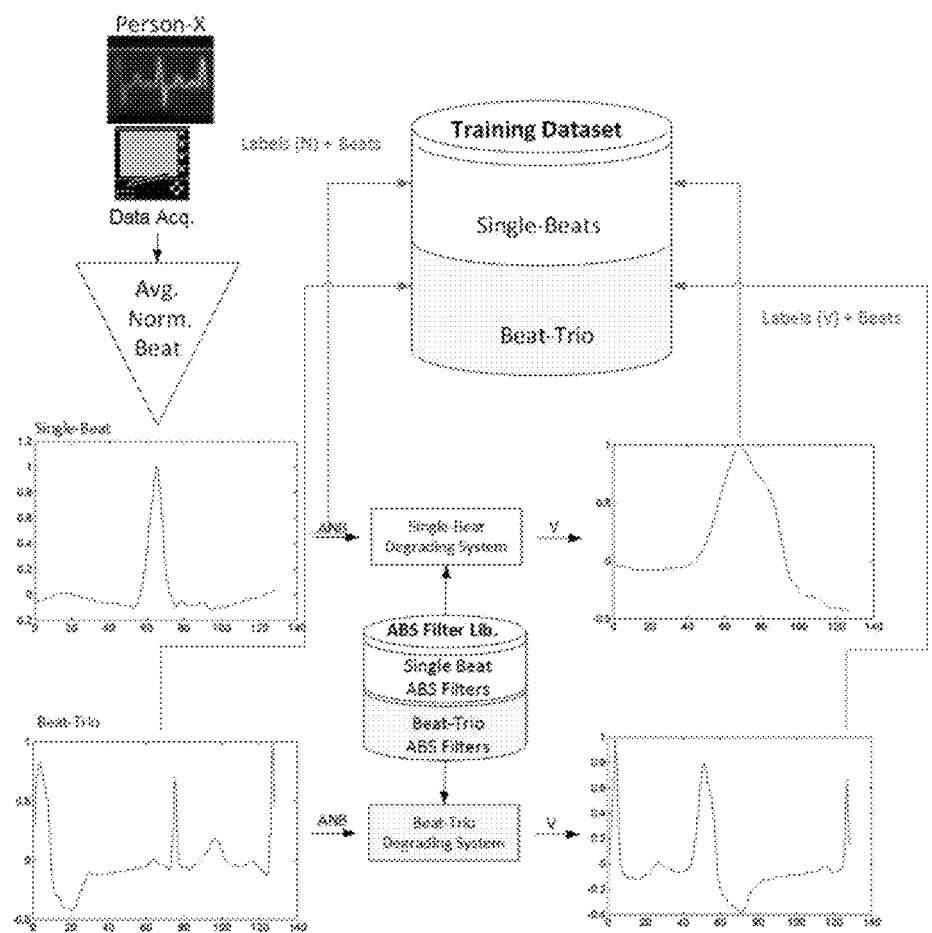
FIG. 7 is a schematic drawing illustrating the generation of personalized training dataset for each subject in the test partition.

After the ABS filter library was formed, the personalized training dataset was generated for each subject in the test partition, as explained earlier and illustrated in FIG. 7. The ANB was formed among the N-beats in the patient-specific part of the record. The beat types were enumerated as follows: N=0, S=1, V=2, Q=3 and F=4.

Figure 11:
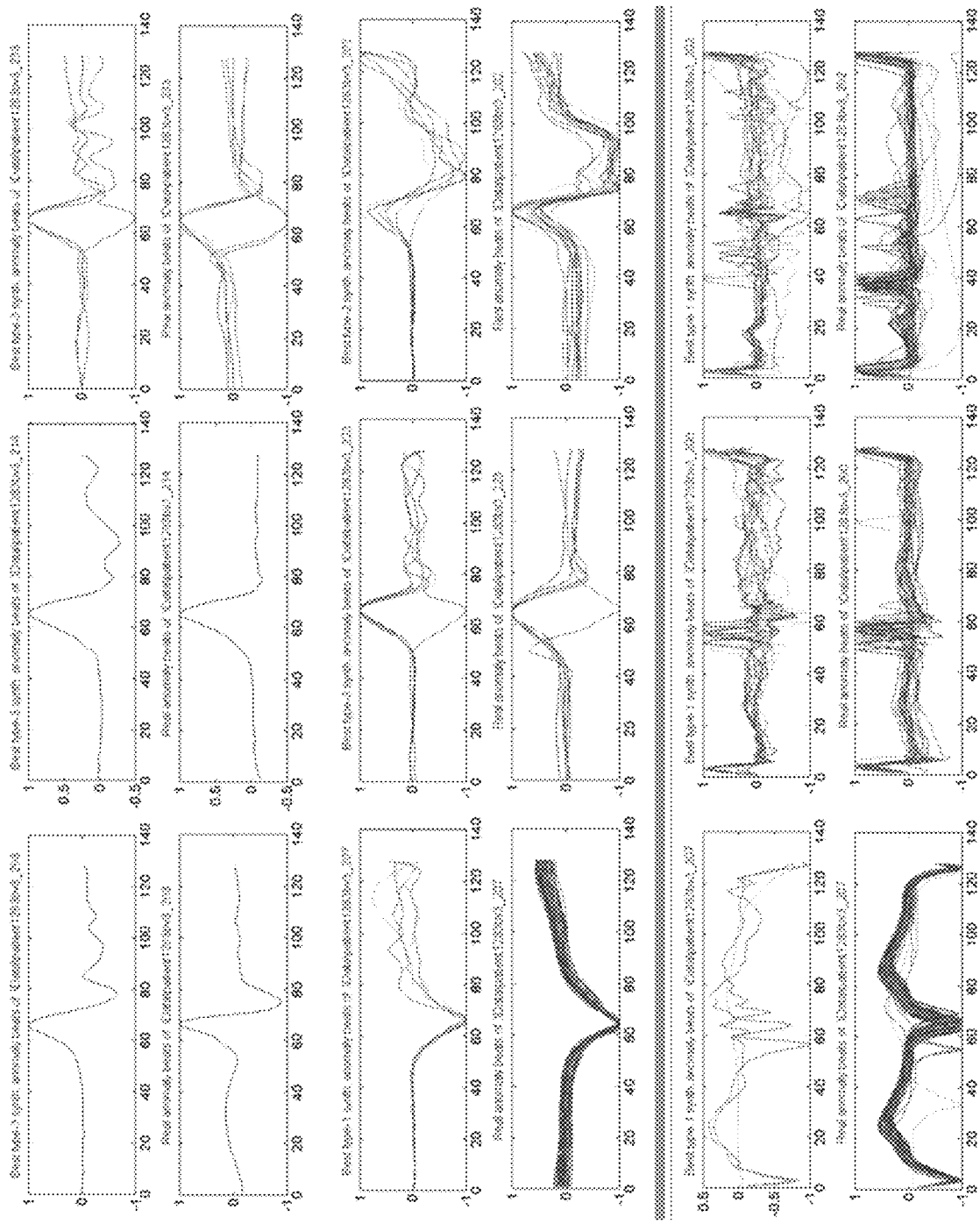
FIG. 11 is a schematic drawing illustrating real abnormal beats and the most similar abnormal beats synthesized by the abnormal beat syntheses filters from the corresponding average normal beat.
Figure 12:
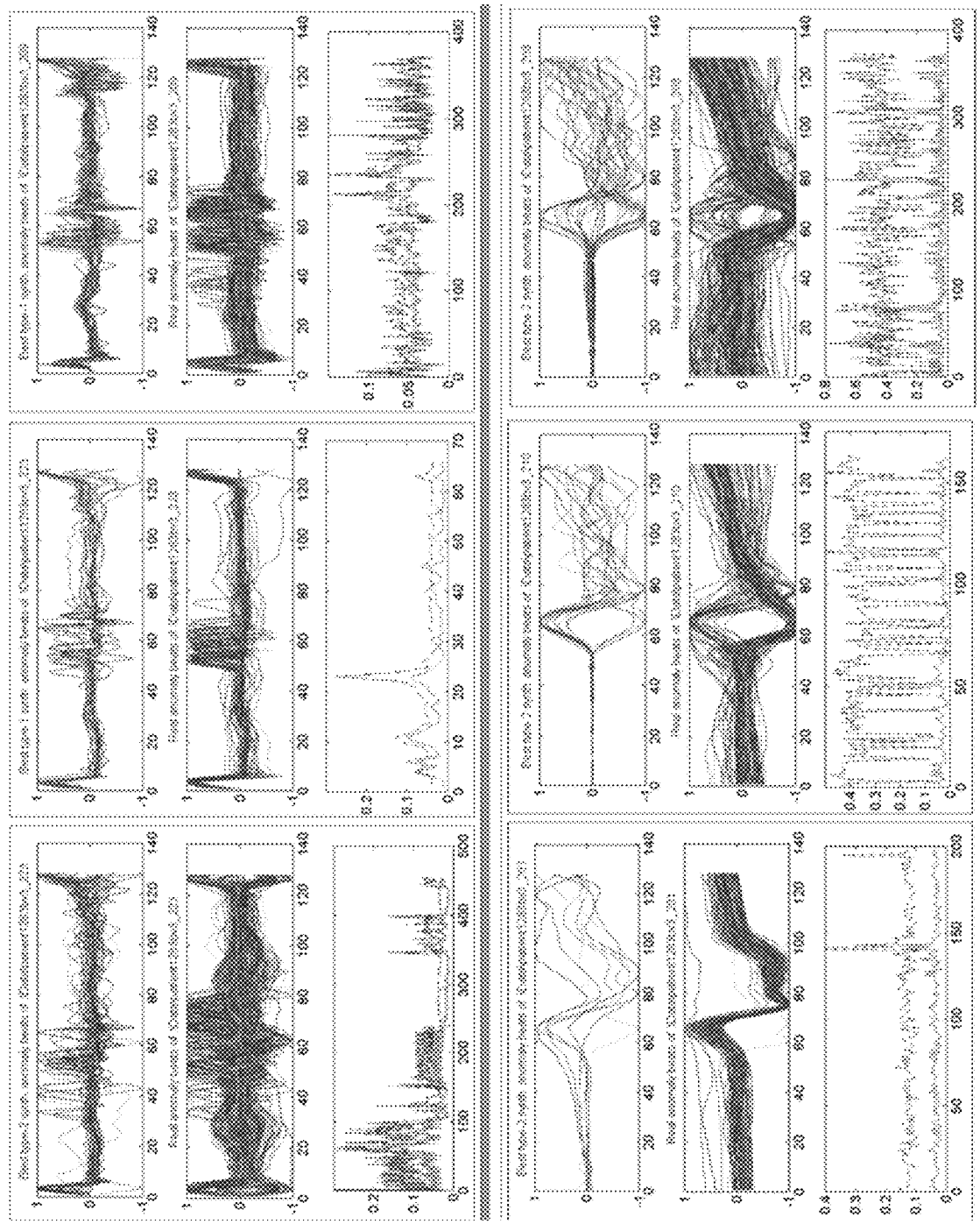
FIG. 12 is a schematic drawing illustrating other examples with a higher number of real abnormal beats.

FIG. 11 shows real abnormal beats in the patient-specific part and the most similar abnormal beats synthesized by the ABS filters from the corresponding ANB. These are the typical results obtained where the abnormal beat pattern (S, V or Q) can be synthesized with a proper ABS filter as long as that filter has already been formed in advance. FIG. 12 shows other examples with a higher number of real abnormal beats (e.g., >60). FIG. 12 also includes MSE plots showing quantitative evaluation. The plots show the similarity scores in terms of minimum MSE between the real abnormal vs. ANB and synthesized beats. Most of the synthesized beats by ABS filters are highly similar to real abnormal beats than the ANB. The opposite is also true. The synthesized abnormal beats are usually more different than the N beats.

Figure 13:
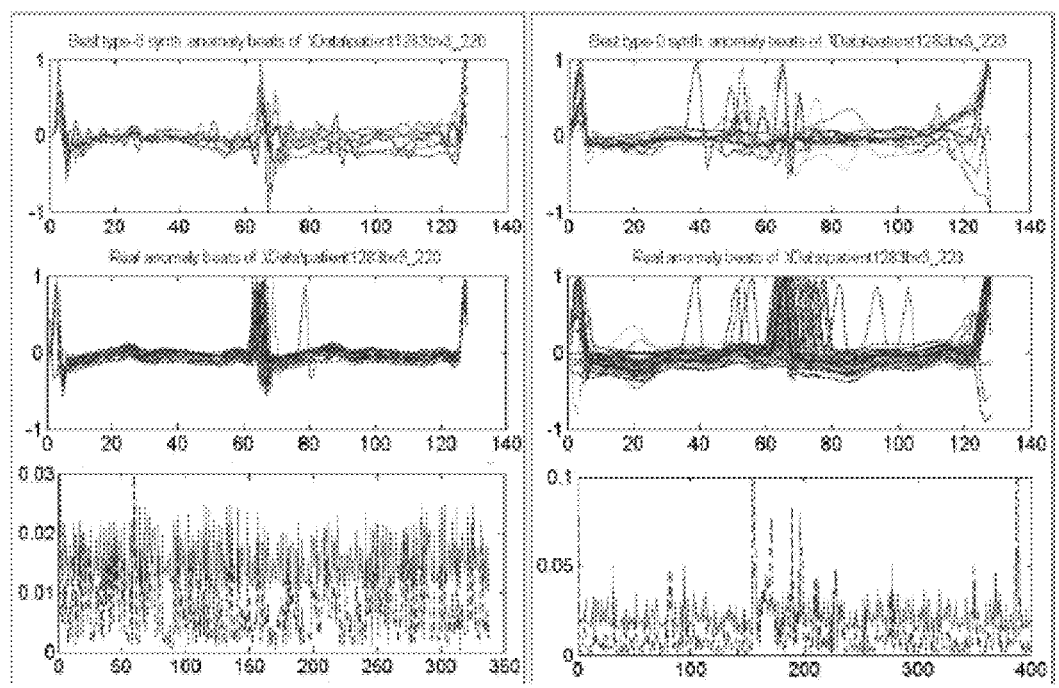
FIG. 13 is a schematic drawing illustrating two plots for a fifth and sixth subject showing the synthesized beats, N beats, and the mean squared error plots in beat-trio representation.

FIG. 13 shows two plots for a fifth and sixth subject showing the synthesized (top) vs. N beats (middle) and the MSE plots (bottom) in beat-trio representation. The majority of N beats are more similar to the ANB than the most similar synthesized beat. However, for some N beats this is not the case especially when the N beat has a similar pattern to S or V beats.

Figure 14:
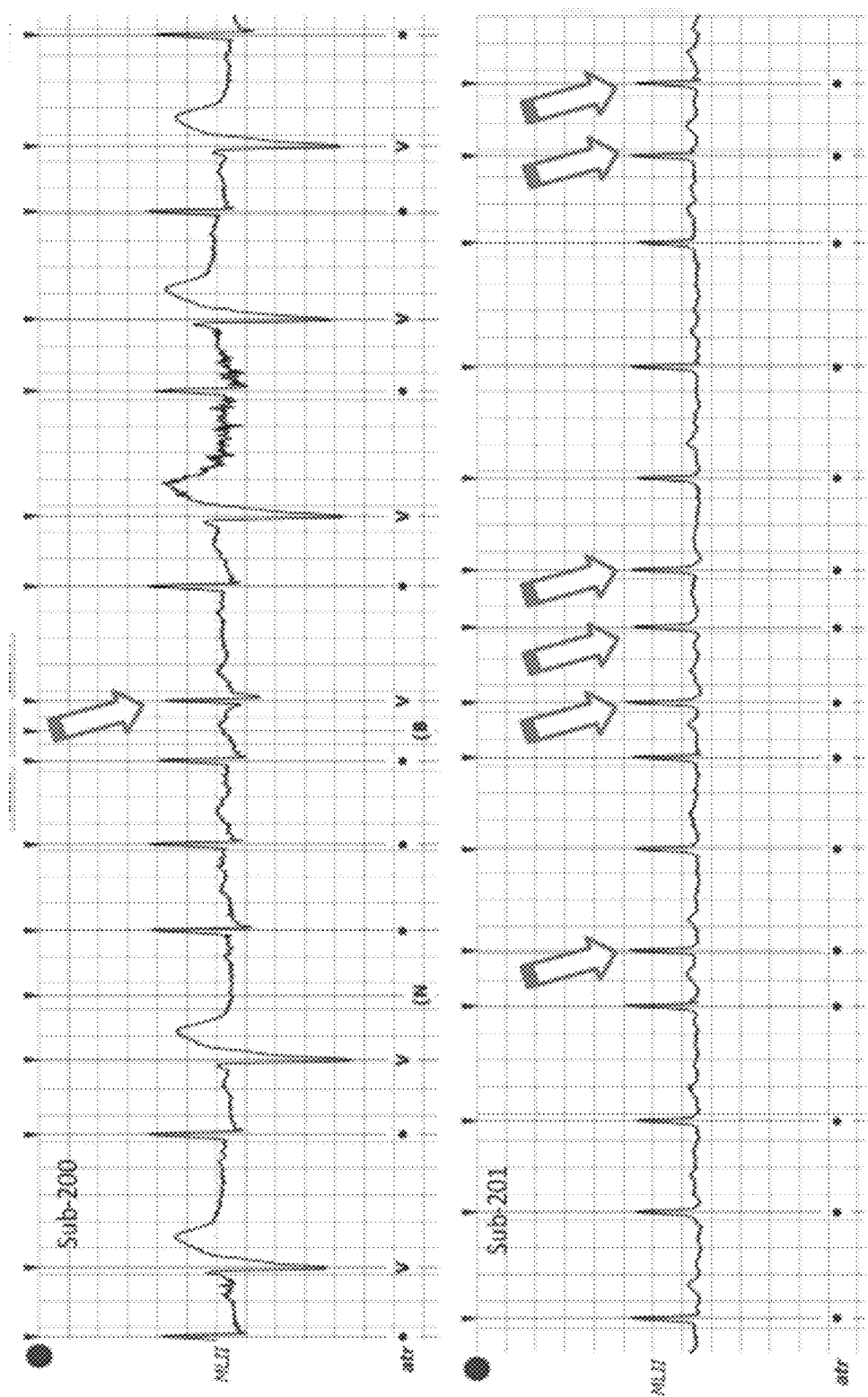
FIG. 14 shows ground-truth labels of seventh and eighth subjects.

FIG. 14 shows ground-truth labels of seventh and eighth subjects. The arrows indicate those beats (V beat for the seventh subject and 6 N beats for the eighth subject) show characteristics of S beats. Such beats have the highest similarity to a (synthesized or real) S beat. In some patients this is also true for the V beats which have high similarities to N beats and vice versa.

Abnormal beat detection is a binary classification problem that assigns beats to either normal (N) or abnormal (S, V, Q, or F). Because this was originally a 5 class problem to compute the two binary detection performance metrics, abnormal beat detection accuracy (Acc) and false alarm rate (FAR), the 5×5 confusion matrix (CM) of each run was cumulated and then a binary (2×2) CM was deduced from the cumulated 5×5 CM.

For example, FIG. 15 shows a parametrized, cumulated CM, where the ground-truth numbers are in the columns. The deduction of this 5×5 CM to 2×2 CM is basically the fusion of the abnormal classes (S, V, F and Q) into a single abnormal class (A), while keeping the normal (N) as the other class. FIG. 16 shows the deducted CM. The number $N_0$ (number of N beats correctly classified) will be the same as in 5×5 CM. $N_X$ is the number of N beats misclassified; therefore, $N_X=N_1+N_2+N_3+N_4$. $A_X$ is the misclassified abnormal beats, or equivalently total number of abnormal beats classified as N beats. Therefore, $A_X=S_1+V_1+F_1+Q_1$. $A_0$ is the correctly classified (detected) beats and is the sum of all numbers in the highlighted block in FIG. 15.

With these definitions, $A_{cc}=A_0/(A_0+A_X)$ and $FAR=N_X/(N_0+N_X)$. Because $N_0+N_X$ and $A_0+A_X$ are the total number of normal and abnormal beats, respectively, $A_{cc}$ and FAR can also be interpreted as the probability of detecting an abnormal beat accurately, and erroneously. 1−Acc is also the probability of missing the detection of an abnormal beat. Therefore, the probability of missing consecutive n abnormal beats will be $P_n=(1-A_{cc})^n$.

FIG. 17 shows the CM cumulated by the classification results of 10 CNNs, each of which was trained in a distinct BP run. FIG. 18 shows the 2×2 CM deducted from FIG. 17. Using the aforementioned performance metrics, one can compute, Acc=80.1% and FAR=0.43%. The average probability of missing the first abnormal beat, therefore, is 0.199 and the average probability of missing all three consecutive abnormal beats is around 0.0079. So detecting one or more abnormal beat(s) among the first three occurrences is highly probable (>99.2%) by using the proposed method. However, the FAR is not insignificant.

The above-described approach achieves the objectives of maintaining a real-time, robust and personalized heart monitoring system for the early detection of cardiac arrhythmias. It is also a fully automatic and unsupervised system as it does not require any manual feedback or verification from a cardiologist to function.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative apparatus and method, and illustrative examples shown and described. Accordingly, departures may be made from such details without departing from the spirit or scope of the applicant's general inventive concept.

What is claimed is:

1. An abnormal heartbeat detector and alert system comprising:
   a sensor configured to contact skin of a user and sense electrical changes on the skin that arise from a heart's electrophysiologic pattern to generate a normal ECG signal;
   a library of abnormal beat synthesis (ABS) filters, wherein each ABS filter corresponds to a specific cause of a cardiac problem;
   at least one processor configured to:
      monitor the normal ECG signal,
      apply at least one ABS filter from the library of ABS filters to the normal ECG signal of the user,
      generate a potential abnormal ECG from the applying of the at least one ABS filter from the library of ABS filters to the normal ECG signal of the user,
      detect a real abnormal heartbeat, and
      generate an alert upon the detecting of the real abnormal heartbeat; and a notification device configured to provide a notification upon receipt of the alert.

2. The abnormal heartbeat detector and alert system of claim 1, wherein the at least one processor is a single processor configured to monitor the normal ECG signal, apply at least one ABS filter from the library of ABS filters to the normal ECG signal of the user to generate the potential abnormal ECG, detect the real abnormal heartbeat, and generate the alert upon detecting the real abnormal heartbeat.

3. The abnormal heartbeat detector and alert system of claim 1, wherein the at least one processor includes at least a first processor and a second processor, wherein the first processor is configured to monitor the normal ECG signal, detect the real abnormal heartbeat, and generate the alert upon detecting the real abnormal heartbeat, and wherein the second processor is to perform at least the steps of applying at least one ABS filter from the library of ABS filters to the normal ECG signal of the user to generate the potential abnormal ECG, create a personal training dataset, train a 1D convolutional neural network over the personal training dataset and upload it to the first processor.

4. The abnormal heartbeat detector and alert system of claim 3, further comprising a personal ECG monitor that includes the sensor, the first processor, and the notification device.

5. The abnormal heartbeat detector and alert system of claim 4, wherein the personal ECG monitor includes at least one of a wrist band and a chest strap.

6. The abnormal heartbeat detector and alert system of claim 1, further comprising a dedicated 1D convolutional neural network configured to train over a personalized dataset comprising the normal ECG signal and the potential abnormal ECG of the person.

7. The abnormal heartbeat detector and alert system of claim 1, wherein the notification device is selected from the group consisting of: a display screen, a speaker, an indicator light, a vibrating device, a printer, and a radio frequency transmitter.

* * * * *